United States Patent
Govari et al.

(10) Patent No.: US 12,262,941 B2
(45) Date of Patent: *Apr. 1, 2025

(54) TEMPERATURE CONTROLLED SHORT DURATION ABLATION WITH MULTIPLE ELECTRODES

(71) Applicant: Biosense Webster (Israel) Ltd., Yokneam (IL)

(72) Inventors: Assaf Govari, Haifa (IL); Andres Claudio Altmann, Haifa (IL); Yaron Ephrath, Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 147 days.

This patent is subject to a terminal disclaimer.

(21) Appl. No.: 18/179,543

(22) Filed: Mar. 7, 2023

(65) Prior Publication Data
US 2023/0200903 A1    Jun. 29, 2023

Related U.S. Application Data

(63) Continuation of application No. 15/994,459, filed on May 31, 2018, now Pat. No. 11,666,379.
(Continued)

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00029* (2013.01);
(Continued)

(58) Field of Classification Search
CPC ...... A61B 18/1206; A61B 2018/00702; A61B 2018/00779; A61B 2018/00797;
(Continued)

(56) References Cited

U.S. PATENT DOCUMENTS

| 5,931,835 A | 8/1999 | Mackey |
| 6,135,998 A | 10/2000 | Palanker |

(Continued)

FOREIGN PATENT DOCUMENTS

| EP | 1645234 A1 | 4/2006 |
| JP | 2004-160084 A | 6/2004 |

(Continued)

OTHER PUBLICATIONS

Office Action from corresponding Japanese Patent Application No. 2022-100947, dated Jun. 20, 2023.
(Continued)

*Primary Examiner* — Michael F Peffley
*Assistant Examiner* — Samantha M Good
(74) *Attorney, Agent, or Firm* — Dergosits & Noah LLP; Todd A. Noah

(57) ABSTRACT

Apparatus, including a catheter configured to be inserted into an organ of a human body. A plurality of electrodes are deployed on the catheter, the electrodes being configured to transfer radiofrequency (RF) ablation energy to tissue of the organ. The apparatus also includes a power supply configured to supply the RF ablation energy at a level of up to 100 W to each of the plurality of electrodes simultaneously, so as to ablate respective sections of the tissue of the organ in contact with the electrodes.

12 Claims, 9 Drawing Sheets

Related U.S. Application Data

(60) Provisional application No. 62/529,158, filed on Jul. 6, 2017.

(52) U.S. Cl.
CPC .......... *A61B 2018/0022* (2013.01); *A61B 2018/00267* (2013.01); *A61B 2018/00273* (2013.01); *A61B 2018/00375* (2013.01); *A61B 2018/00577* (2013.01); *A61B 2018/00654* (2013.01); *A61B 2018/00708* (2013.01); *A61B 2018/00797* (2013.01); *A61B 2018/00821* (2013.01); *A61B 2018/00875* (2013.01); *A61B 2018/00928* (2013.01); *A61B 2018/1467* (2013.01)

(58) Field of Classification Search
CPC .. A61B 2018/00821; A61B 2018/1467; A61B 18/1492
See application file for complete search history.

(56) References Cited

U.S. PATENT DOCUMENTS

| | | | |
|---|---|---|---|
| 6,319,249 | B1 | 11/2001 | Tollner |
| 8,357,152 | B2 | 1/2013 | Govari et al. |
| 10,441,354 | B2 * | 10/2019 | Govari ............... A61B 18/1492 |
| 10,441,357 | B2 | 10/2019 | Moeskops et al. |
| 10,893,904 | B2 * | 1/2021 | Govari ............... A61B 18/1492 |
| 11,666,379 | B2 * | 6/2023 | Govari ............... A61B 18/1492 606/41 |
| 2001/0008967 | A1 | 7/2001 | Sherman |
| 2001/0020166 | A1 | 9/2001 | Daly et al. |
| 2002/0156472 | A1 | 10/2002 | Lee et al. |
| 2002/0161361 | A1 | 10/2002 | Sherman et al. |
| 2003/0236455 | A1 | 12/2003 | Swanson et al. |
| 2004/0049181 | A1 | 3/2004 | Stewart et al. |
| 2008/0161797 | A1 | 7/2008 | Wang et al. |
| 2008/0188844 | A1 | 8/2008 | McGreevy et al. |
| 2009/0036882 | A1 | 2/2009 | Webster et al. |
| 2010/0057072 | A1 | 3/2010 | Roman et al. |
| 2011/0130648 | A1 | 6/2011 | Beeckler et al. |
| 2012/0157890 | A1 * | 6/2012 | Govari ............... A61B 18/20 601/3 |
| 2014/0066921 | A1 | 3/2014 | Coe et al. |
| 2015/0272655 | A1 | 10/2015 | Condie et al. |
| 2015/0272667 | A1 | 10/2015 | Govari et al. |
| 2017/0027640 | A1 | 2/2017 | Kunis et al. |
| 2017/0049513 | A1 | 2/2017 | Cosman et al. |

FOREIGN PATENT DOCUMENTS

| | | |
|---|---|---|
| JP | 2005-501596 A | 1/2005 |
| JP | 2009-500052 A | 1/2009 |
| KR | 10-2013-0108401 | 10/2013 |
| WO | 2003020144 A1 | 3/2003 |
| WO | 2007001981 A2 | 1/2007 |
| WO | 2012061161 A1 | 5/2012 |

OTHER PUBLICATIONS

Office Action from Korean Patent Application No. 10-2018-0147061, dated Sep. 26, 2023.
Search Report from corresponding European Patent Application No. 18181833.7, dated Apr. 1, 2019.
Search Report from corresponding Japanese Patent Application No. 2018128077, dated Mar. 18, 2022.

* cited by examiner

TEMPERATURE CONTROLLED SHORT DURATION ABLATION WITH MULTIPLE ELECTRODES

CROSS-REFERENCE TO RELATED APPLICATION

This application is a continuation application of U.S. application Ser. No. 15/994,459, filed May 31, 2018, now U.S. Pat. No. 11,666,379, which claims the benefit of U.S. Provisional Patent Application 62/529,158, filed 6 Jul. 2017, both of which are incorporated herein by reference.

FIELD OF THE INVENTION

This invention relates generally to surgery, and specifically to surgery using radiofrequency ablation.

BACKGROUND OF THE INVENTION

Radiofrequency (RF) ablation is a treatment modality that kills unwanted tissue by heat. Starting with cardiac arrhythmia treatment in the 1980s, RF ablation has found clinical application in a number of diseases, and is now the treatment of choice for certain types of cardiac arrhythmia, and certain cancers. During RF ablation, an electrode is inserted into proximity with the target region under medical imaging guidance. Tissue surrounding the electrode in the target region is destroyed by heating via RF electric current.

U.S. Patent Application 2003/0236455 to Swanson et al., describes a probe assembly for mapping and ablating pulmonary vein tissue. The probe assembly includes an expandable and collapsible basket assembly having multiple splines. One or more of the splines carry one or more electrodes adapted to sense electrical activity in the pulmonary vein tissue.

U.S. Patent Application 2014/0066921 to Coe et al., describes balloon catheter neuromodulation systems. The application refers to modulating (e.g., disrupting, ablating, stimulating) the nerves by mechanical compression, energy delivery, or fluid delivery.

U.S. Pat. No. 5,931,835 to Mackey, describes a radio frequency energy delivery system for multipolar electrode catheters. It is stated that the power, voltage, or temperature delivered to multiple electrodes may be dynamically controlled.

EP Patent Application 1,645,234 to Buysse et al., describes an electrosurgical system employing multiple electrodes. The system employs multiple electrodes for producing large ablation volumes in tissue.

U.S. Patent Application 2002/0161361 to Sherman et al., describes an RF ablation system using electrodes and having automatic temperature control. It is stated that a select number of the electrodes have a temperature sensing device associated with them for providing a temperature signal indicative of the temperature at the interface between the electrode and tissue.

U.S. Patent Application 2001/0020166 to Daly et al., describes a system for simultaneous unipolar multi-electrode ablation. The system is stated to ablate tissue using unipolar RF energy simultaneously delivered to multiple electrodes.

U.S. Pat. No. 6,319,249 to Tollner, describes an ablation catheter with, inter alia, a plurality of ablation electrodes, at least one energy source, and switching elements for connecting the electrodes to the energy source.

U.S. Patent Application 2008/0161797 to Wang et al., describes ablation catheter electrodes having multiple thermal sensors. The electrodes are stated to contain two or more thermal sensors at different positions within the electrode.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE DISCLOSURE

An embodiment of the present invention provides apparatus, including:
a catheter configured to be inserted into an organ of a human body;
a plurality of electrodes deployed on the catheter, the electrodes being configured to transfer radiofrequency (RF) ablation energy to tissue of the organ; and
a power supply configured to supply the RF ablation energy at a level of up to 100 W to each of the plurality of electrodes simultaneously, so as to ablate respective sections of the tissue of the organ in contact with the electrodes.

In a disclosed embodiment the plurality of electrodes includes up to twelve electrodes, and the power supply is configured to provide up to 1.2 kW of radiofrequency power.

In a further disclosed embodiment the apparatus includes a plurality of temperature sensors each coupled to measure a respective temperature of one of the plurality of electrodes, and the power supply is configured, when the respective temperature of the one of the plurality of electrodes in contact with one of the sections of tissue exceeds a selected maximum temperature, to reduce the level of power of the RF ablation energy supplied to the one of the plurality of electrodes.

In a yet further disclosed embodiment the apparatus includes a processor which is coupled to the power supply and which is configured to simultaneously measure a respective impedance to the RF ablation energy for each of the plurality of electrodes, and, when a change in the impedance to one of the plurality of electrodes in contact with one of the sections of tissue exceeds a preset value, to halt supply of the RF ablation energy from the power supply to the one of the plurality of electrodes.

The catheter may include a balloon catheter. Alternatively, the catheter may include a basket catheter.

There is further provided, according to an embodiment of the present invention, apparatus, including:
a catheter configured to be inserted into an organ of a human body;
a first electrode and a second electrode deployed on the catheter, the electrodes being configured to transfer radiofrequency (RF) ablation energy to tissue of the organ;
a first temperature sensor coupled to measure a first temperature of the first electrode;
a second temperature sensor coupled to measure a second temperature of the second electrode;
a power supply configured to provide the RF ablation energy;
a switch connected to the power supply and configured to direct the RF ablation energy to one of the first and second electrodes; and a processor configured, while the power supply is providing the RF ablation energy via the switch to the first electrode, to monitor the first and second temperatures and, responsively to the monitored temperatures, to toggle the switch so as direct the RF ablation energy to one of the first and second electrodes.

In an alternative embodiment the processor is configured, upon sensing that the first temperature exceeds a predefined ablation temperature threshold while the second temperature does not exceed the ablation temperature threshold, to toggle the switch so as to direct the RF ablation energy to the second electrode.

In a further alternative embodiment the processor is configured to monitor a first time for ablation via the first electrode and a second time for ablation via the second electrode, and, responsively to the monitored times, to toggle the switch so as direct the RF ablation energy to one of the first and second electrodes. Typically, the processor is configured, upon sensing that the first time for ablation equals or exceeds a preset first time for ablation for the first electrode while the second time for ablation is less than a preset second time for ablation for the second electrode, to toggle the switch so as to direct the RF ablation energy to the second electrode.

In a yet further alternative embodiment the first electrode is configured to transfer the RF ablation energy at a first power level, and the second electrode is configured to transfer the RF ablation energy at a second power level, and the power supply is configured to supply power to the electrodes at a level no greater than a maximum of the first and second power levels.

The catheter may be a balloon catheter. Alternatively, the catheter may be a basket catheter.

There is further provided, according to an embodiment of the present invention, a method, including:
inserting a catheter into an organ of a human body;
deploying a plurality of electrodes on the catheter, the electrodes being configured to transfer radiofrequency (RF) ablation energy to tissue of the organ; and
supplying with a power supply the RF ablation energy at a level of up to 100 W to each of the plurality of electrodes simultaneously, so as to ablate respective sections of the tissue of the organ in contact with the electrodes.

There is further provided, according to an embodiment of the present invention, a method, including:
inserting a catheter into an organ of a human body;
deploying a first electrode and a second electrode on the catheter, the electrodes being configured to transfer radiofrequency (RF) ablation energy to tissue of the organ;
coupling a first temperature sensor to measure a first temperature of the first electrode;
coupling a second temperature sensor to measure a second temperature of the second electrode;
configuring a power supply to provide the RF ablation energy;
connecting a switch to the power supply and configuring the switch to direct the RF ablation energy to one of the first and second electrodes; and
while the power supply is providing the RF ablation energy via the switch to the first electrode, monitoring the first and second temperatures and, responsively to the monitored temperatures, toggling the switch so as direct the RF ablation energy to one of the first and second electrodes.

The present disclosure will be more fully understood from the following detailed description of the embodiments thereof, taken together with the drawings, in which:

DETAILED DESCRIPTION OF EMBODIMENTS

Overview

Figure 1:
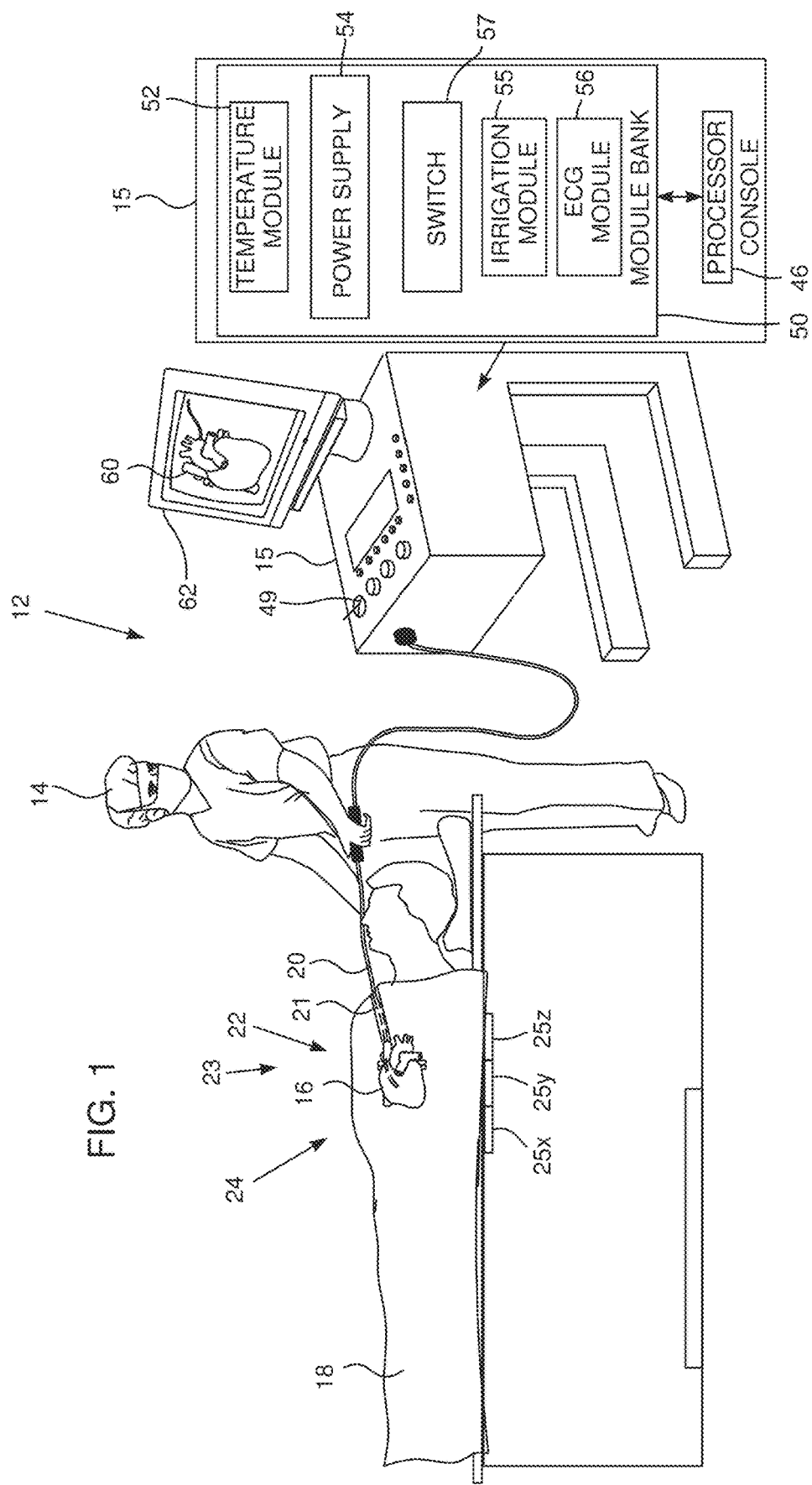
FIG. 1 is a schematic illustration of an invasive medical procedure using apparatus, according to an embodiment of the present invention.

In embodiments of the present invention, a catheter, having a plurality of electrodes deployed thereon, is inserted into an organ, typically the heart, of a human body. The electrodes are configured to transfer radiofrequency (RF) ablation energy to tissue of the organ.

In a first embodiment of the invention, a power supply supplies the RF ablation energy at a level of up to 100 W to each of the plurality of electrodes simultaneously, so as to ablate respective sections of the tissue of the organ in contact with the electrodes. During such simultaneous ablation, careful monitoring of the temperature and impedance at each electrode separately allows embodiments of the present invention to perform multiple tissue ablations at the powers of up to 100 W at each electrode without adverse effects on the tissue. The high powers enable an overall ablation session for the multiple ablations to be shortened to times typically of no more than 10 s.

In a second embodiment of the invention, the plurality of electrodes comprise a first electrode and a second electrode. A first temperature sensor measures a first temperature of the first electrode, and a second temperature sensor measures a second temperature of the second electrode. A power supply provides the RF ablation energy, and a switch is connected to the power supply and is configured to direct the RF ablation energy to one of the first and second electrodes. A processor is configured, while the power supply is providing the RF ablation energy via the switch to the first electrode, to monitor the first and second temperatures and, responsively to the monitored temperatures, to toggle the switch so as direct the RF ablation energy to one of the first and second electrodes. Switching the RF energy between the electrodes, depending on the temperatures of the electrodes, ensures efficient utilization of a power supply that may be unable to provide high powers to both electrodes simultaneously, due to a maximum power rating of the power supply.

Detailed Description

In the following description, like elements in the drawings are identified by like numerals, and like elements are differentiated as necessary by appending a letter to the identifying numeral.

FIG. 1 is a schematic illustration of an invasive medical procedure using apparatus 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it is understood that embodiments of the present invention are not merely applicable to this specific procedure, and may include substantially any procedure on biological tissue or on non-biological materials.

In order to perform the ablation, medical professional 14 inserts a probe 20 into a sheath 21 that has been pre-positioned in a lumen of the patient. Sheath 21 is positioned so that a distal end 22 of probe 20 enters the heart of the patient. A balloon catheter 24, which is described in more detail below with reference to FIGS. 2-5, is deployed through a lumen 23 of the probe 20, and exits from distal end 22 of the probe 20.

As shown in FIG. 1, apparatus 12 is controlled by a system processor 46, which is located in an operating console 15 of the apparatus. Console 15 comprises controls 49 which are used by professional 14 to communicate with the processor. During the procedure, the processor 46 typically tracks a location and an orientation of the distal end 22 of the probe 20, using any method known in the art. For example, processor 46 may use a magnetic tracking method, wherein magnetic transmitters 25X, 25Y and 25Z external to patient 18 generate signals in one or more coils positioned in the distal end of the probe 20. The CARTO® system available from Biosense Webster, of 33 Technology Drive, Irvine, CA 92618, uses such a tracking method.

The software for the processor 46 may be downloaded to the processor in electronic form, over a network, for example. Alternatively or additionally, the software may be provided on non-transitory tangible media, such as optical, magnetic, or electronic storage media. The tracking of the distal end 22 is typically displayed on a three-dimensional representation 60 of the heart of patient 18 on a screen 62.

In the description herein processor 46 is assumed to be formed from any suitable integrated circuits, including, but not limited to, an ASIC (application specific integrated circuit), an FPGA (field-programmable gate array), an MCU (microcontroller unit), and a CPU.

In order to operate apparatus 12, the processor 46 communicates with a module bank 50, which has a number of modules used by the processor to operate the apparatus. Thus, the bank 50 comprises a temperature module 52, a power supply 54, a switch 57, an irrigation module 55, and an electrocardiograph (ECG) module 56, the functions of which are described below. Bank 50 typically comprises other modules, such as a force module for measuring the force on the distal end 22, and a tracking module for operating the tracking method used by the processor 46. For simplicity, such other modules are not illustrated in FIG. 1. The modules may comprise hardware as well as software elements.

Figure 2:
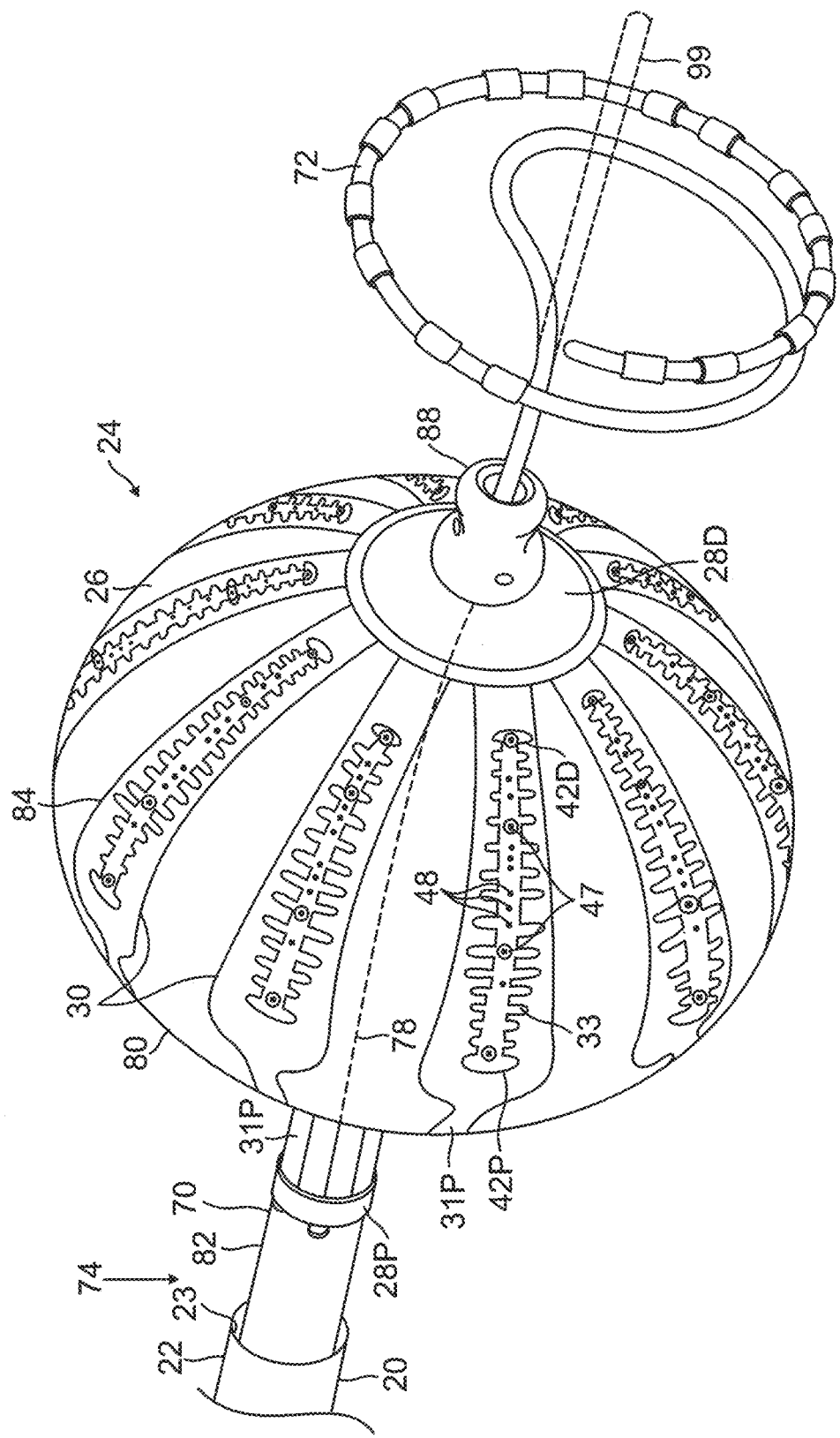
FIG. 2 is a schematic perspective view of a balloon catheter in its inflated configuration, according to an embodiment of the present invention.
Figure 3:
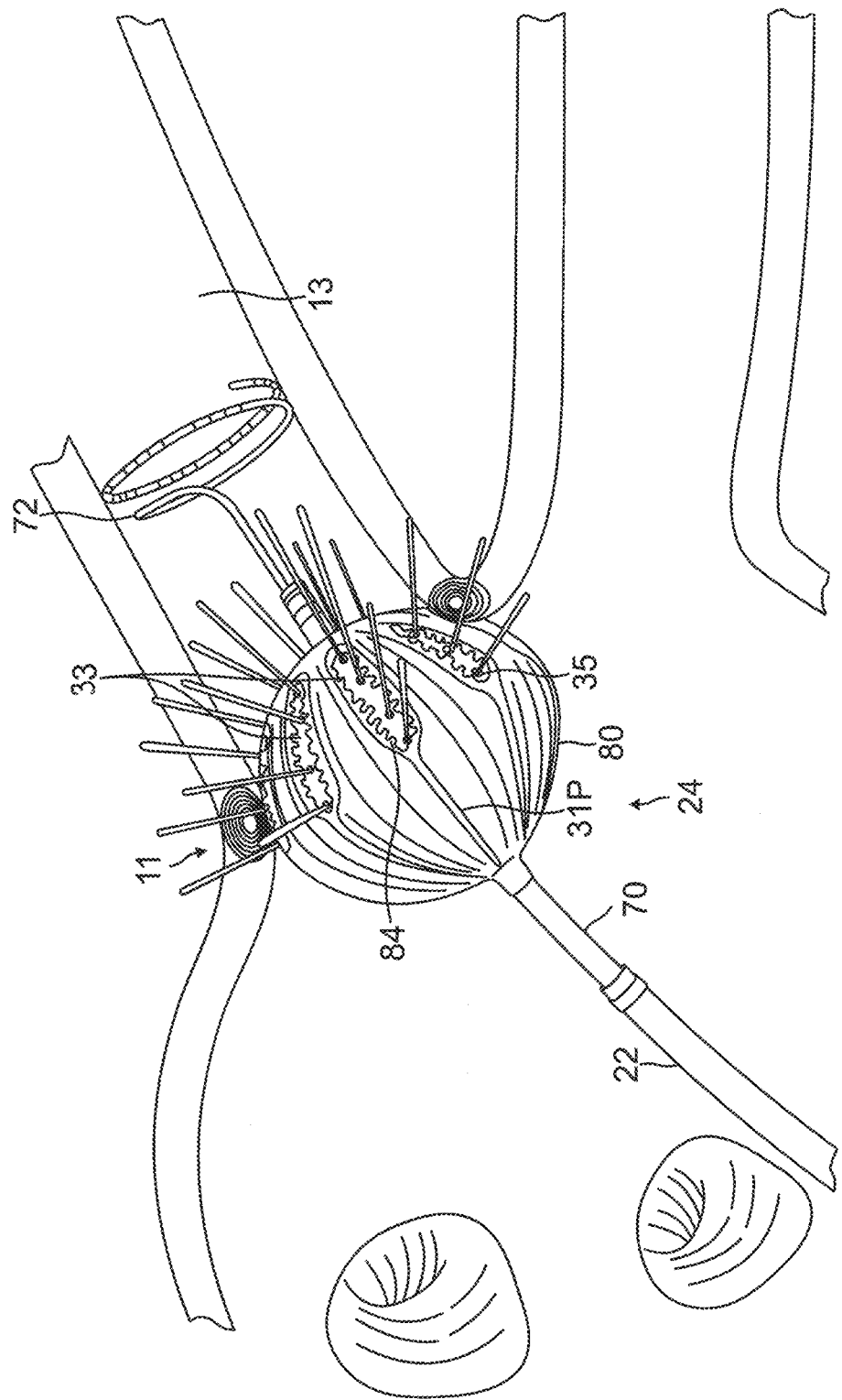
FIG. 3 is a schematic view of the balloon catheter deployed in a pulmonary vein, according to an embodiment of the present invention.

FIG. 2 is a schematic perspective view of the balloon catheter 24 in its inflated configuration, and FIG. 3 is a schematic view of the balloon catheter deployed in a pulmonary vein, according to an embodiment of the present invention. In a disclosed embodiment, where the balloon catheter 24 is used to ablate an ostium 11 of a lumen, such as a pulmonary vein 13, as shown in FIG. 3, the balloon catheter 24 is supported by a tubular shaft 70 having a proximal shaft portion 82 and a distal shaft end 88. The shaft 70 comprises a hollow central tube 74, which permits a support catheter to pass therethrough and through the distal shaft end 88. The support catheter may be a focal linear catheter or a lasso catheter 72, as illustrated. The lasso catheter 72 may be inserted into the pulmonary vein (PV) to position the balloon catheter 24 correctly with respect to the ostium prior to ablation of the ostium. The distal lasso portion of the catheter 72 is typically formed of shape-memory retentive material such as nitinol.

It is understood that the balloon catheter 24 may also be supported by a linear or focal catheter 99 (as shown in broken lines in FIG. 2) in the PV or elsewhere in the heart. The focal catheter 99 may include a force sensor at its distal tip. Suitable force sending distal tips are disclosed in U.S. Pat. No. 8,357,152, issued on Jan. 22, 2013 to Govari et al., titled CATHETER WITH PRESSURE SENSING, and in U.S. Patent Application 2011/0130648, to Beeckler et al., filed Nov. 30, 2009, titled CATHETER WITH PRESSURE MEASURING TIP, the entire contents of both of which are incorporated herein by reference. Any catheter used in conjunction with the balloon catheter may have features and functions, including, for example, pressure sensing, ablation, diagnostic, e.g., navigation and pacing.

An inflatable balloon 80 of the balloon catheter 24 has an exterior wall or membrane 26 of a bio-compatible material, for example, formed from a plastic such as polyethylene terephthalate (PET), polyurethane or PEBAX®. The shaft 70 and the distal shaft end 88 define a longitudinal axis 78 of the balloon 80. The balloon 80 is deployed, in a collapsed uninflated configuration, via the lumen 23 of the probe 20, and may be inflated after exiting from the distal end 22. The balloon 80 may be inflated and deflated by injection and expulsion of a fluid such as saline solution through the shaft 70. The membrane 26 of the balloon 80 is formed with irrigation pores or apertures 27 (shown in FIG. 5) through which the fluid can exit from the interior of the balloon 80 to outside the balloon for cooling the tissue ablation site at the ostium. While FIG. 3 shows fluid exiting the balloon 80 as jet streams, it is understood that the fluid may exit the balloon with any desired flow rate and/or pressure, including a rate where the fluid is seeping out of the balloon.

The membrane 26 supports and carries a combined electrode and temperature sensing member which is constructed as a multi-layer flexible circuit electrode assembly 84. The "flex circuit electrode assembly" 84 may have many different geometric configurations. In the illustrated embodiment, the flex circuit electrode assembly 84 has a plurality of radiating leaves or strips 30.

Figure 4:
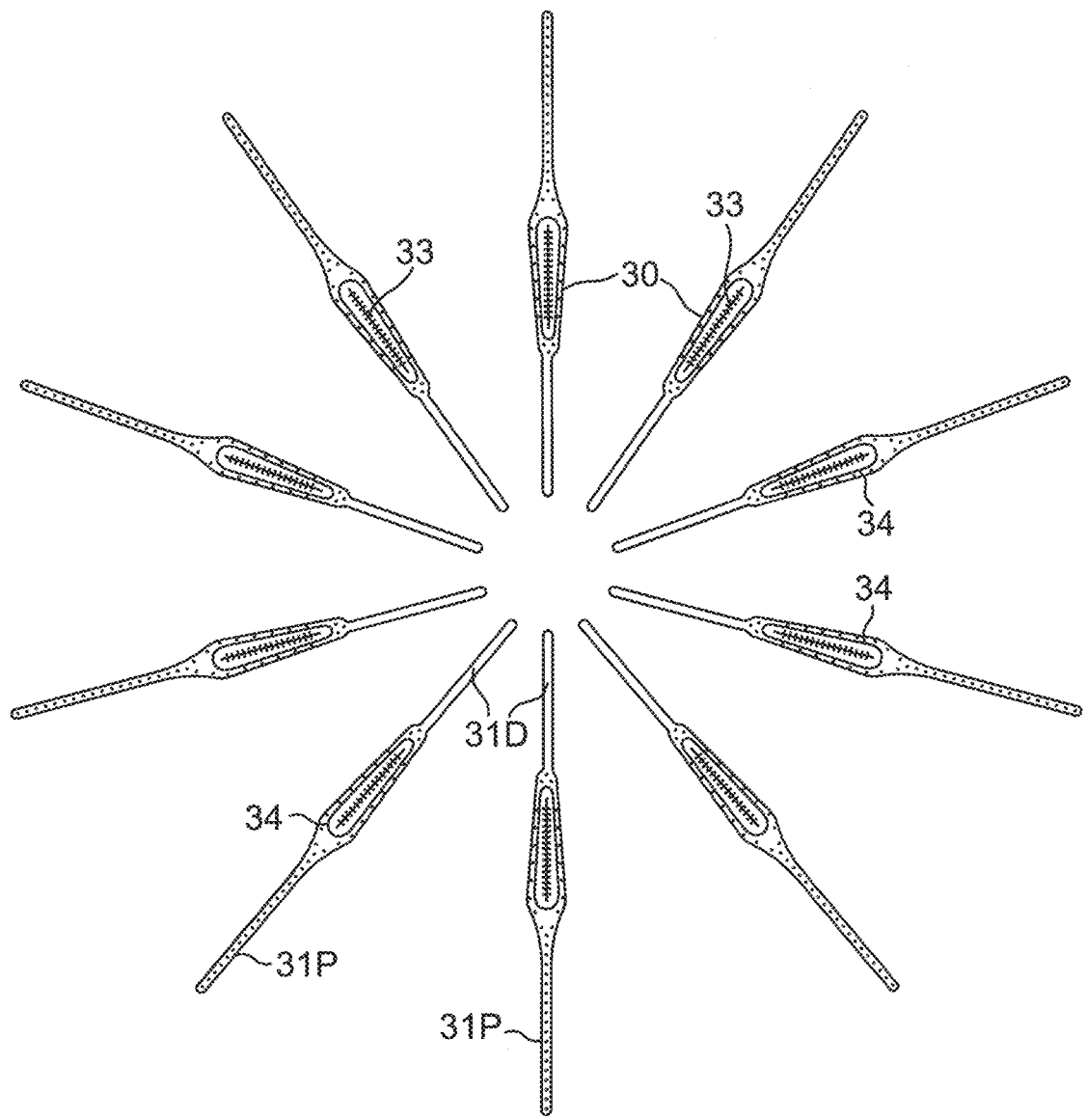
FIG. 4 is a schematic view of a plurality of leaves of flexible circuit assemblies, according to an embodiment of the present invention.

FIG. 4 is a schematic view of a plurality of leaves 30, according to an embodiment of the present invention. The leaves 30 are evenly distributed about the distal end 88 and the balloon 80. Each leaf has wider proximal portion that gradually tapers to a narrower distal portion. FIG. 4 shows, by way of example, ten radiating leaves 30, but it will be understood that embodiments of the present invention may have more or fewer than ten leaves. In one embodiment, referred to below, there are twelve leaves 30.

With reference to FIGS. 2 and 4, each leaf 30 has a proximal tail 31P and a distal tail 31D. The proximal tail 31P is tucked under and fastened to the catheter 24 by a proximal ring 28P mounted on the proximal shaft portion 82 of the shaft 70. The distal tail 31D is tucked under and fastened to the catheter 24 by a distal ring (not shown). Either or both sets of tails 31D and 31P may be further covered by a respective semispherical cap, such as distal cap 28D. One or more contact electrodes 33 on each leaf come into galvanic contract with the ostium 11 during an ablation procedure, during which electrical current flows from the contact electrodes 33 to the ostium 11, as shown in FIG. 3. In the description, electrodes 33 are differentiated as necessary by appending a letter to the identifying numeral, so that there are electrodes 33A, 33B, . . . .

Figure 5:
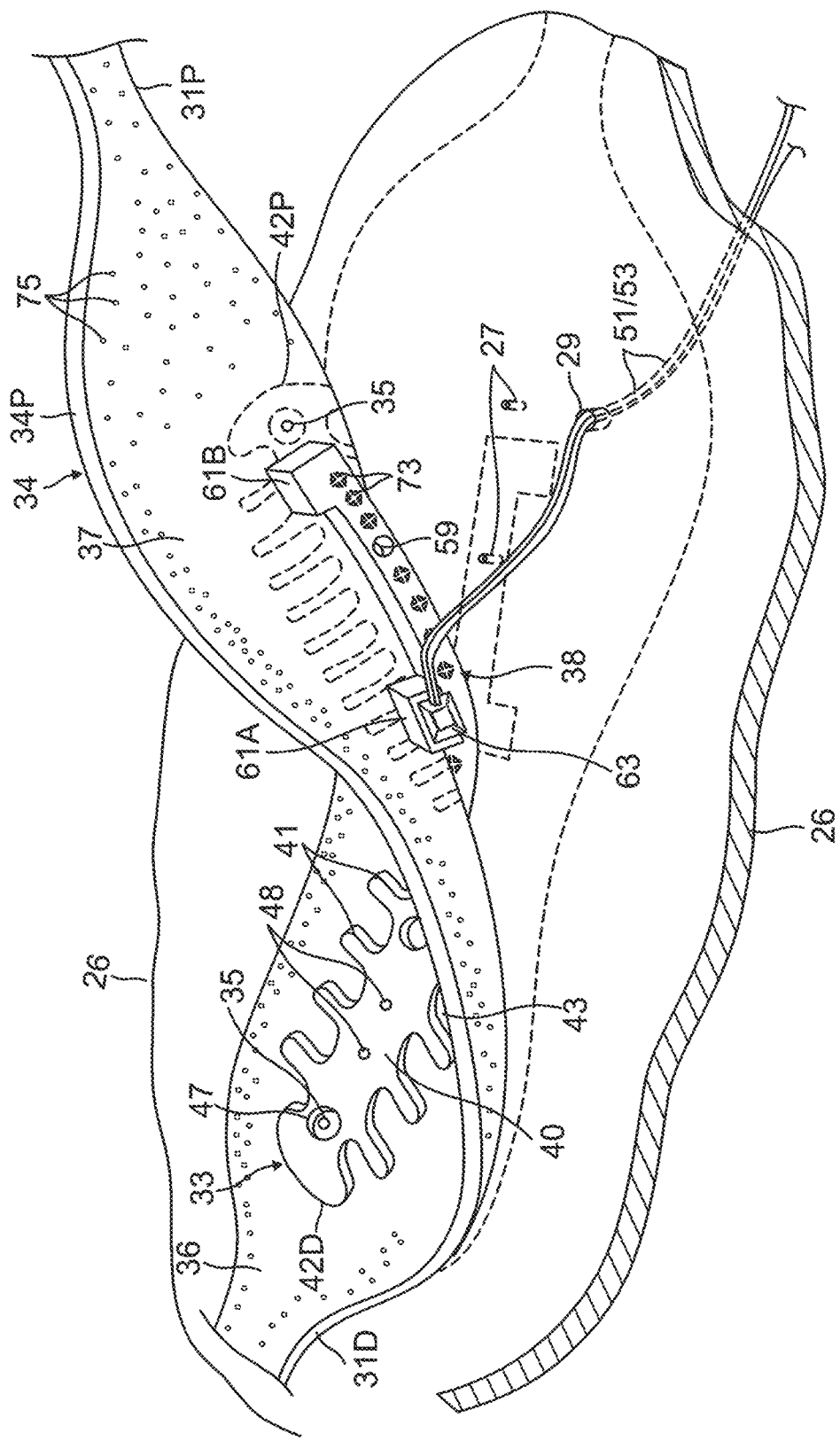
FIG. 5 is a schematic perspective view of a flexible circuit assembly partly lifted from the balloon catheter according to an embodiment of the present invention.

FIG. 5 is a schematic perspective view of a flexible circuit assembly partly lifted from the balloon catheter according to an embodiment of the present invention. For simplicity, the flex circuit electrode assembly 84 is described with respect to one of its leaves 30 as shown in FIG. 5, although it is understood that the following description may apply to each leaf of the assembly. The flex circuit electrode assembly 84 includes a flexible and resilient sheet substrate 34, constructed of a suitable bio-compatible materials, for example, polyimide. In some embodiments, the sheet substrate 34 has a greater heat resistance (or a higher melting temperature) compared to that of the balloon membrane 26. In some embodiments, the substrate 34 is constructed of a thermoset material having a decomposition temperature that is higher than the melting temperature of the balloon membrane 26 by approximately 100° C. or more.

The substrate 34 is formed with one or more irrigation pores or apertures 35 that are in alignment with the irrigation apertures 35 of the balloon member 26 so that fluid passing through the irrigation apertures 35 can pass to the ablation site on the ostium.

The substrate 34 has a first or outer surface 36 facing away from the balloon membrane 26, and a second or inner surface 37 facing the balloon membrane 26. On its outer surface 36, the substrate 34 supports and carries the contact electrodes 33 adapted for tissue contact with the ostium. On its inner surface 37, the substrate 34 supports and carries a wiring electrode 38. The contact electrode 33 delivers RF energy, supplied by power supply 54, to the ostium during ablation and is connected to a thermocouple junction (described in more detail below) for temperature sensing of the ostium. In the illustrated embodiment, the contact electrode 33 has a longitudinally elongated portion 40 and a plurality of thin transversal linear portions or fingers 41 extending generally perpendicularly from each lateral side of the elongated portion 40 between enlarged proximal and distal ends 42P and 42D, generally evenly spaced therebetween. The elongated portion 40 has a greater width and each of the fingers has a generally uniform lesser width. Accordingly, the configuration or trace of the contact electrode 33 resembles a "fishbone."

Formed within the contact electrode 33 are one or more exclusion zone 47, each surrounding an irrigation aperture 27 formed in the substrate 26. The exclusion zones 47 are voids purposely formed in the contact electrode 33, as explained in detail further below, so as to avoid damage to the contact electrode 33 during construction of the electrode assembly 84 in accommodating the irrigation apertures 27 at their locations and in their function.

Also formed in the contact electrode 33 are one or more conductive blind vias 48 which are conductive or metallic formations that extend through through-holes in the substrate 34 and are configured as electrical conduits connecting the contact electrode 33 on the outer surface 36 and the wiring electrode 38 on the inner surface 37. It is understood that "conductive" is used herein interchangeably with "metallic" in all relevant instances.

Attached, e.g., by a solder weld 63, to an active solder pad portion 61A of electrode 38 are a wire pair, e.g., a constantan wire 51 and a copper wire 53. The copper wire 53 provides a lead wire to the wiring electrode 33, and the copper wire 53 and the constantan wire 51 provide a thermocouple whose junction is at solder weld 63, so that weld 63 is also referred to herein as thermocouple junction 63. Junction 63 acts as temperature sensor, and is also referred to herein as sensor 63, and the sensors are differentiated as necessary by appending a letter to the identifying numeral, so that there are sensors 63A, 63B, . . . . Thus, for each electrode 33A, 33B, . . . , there is a respective temperature sensor 63A, 63B, . . . .

The wire pair 51/53 is passed through a through-hole 29 formed in the membrane 26. It is understood that, in other embodiments in the absence of the through-hole 29, the wire pair 51/53 may run between the membrane 26 and the substrate 34 and further proximally between the membrane 26 and the proximal tail 31P until the wire pair 51/53 enters the tubular shaft 70 via another through-hole (not shown) formed in the tubular shaft sidewall closer to the proximal ring 28.

The flex circuit electrode assembly 84, including the leaves 30 and the tails 31P and 31D, is affixed to the balloon membrane 26 such that the outer surface 36 of the substrate 34 is exposed and the inner surface 37 of the substrate 34 is affixed to the balloon membrane 26, with the wiring electrode 38 and wire pair 51/53 sandwiched between the substrate 34 and the balloon membrane 26.

First Embodiment

Figure 6:
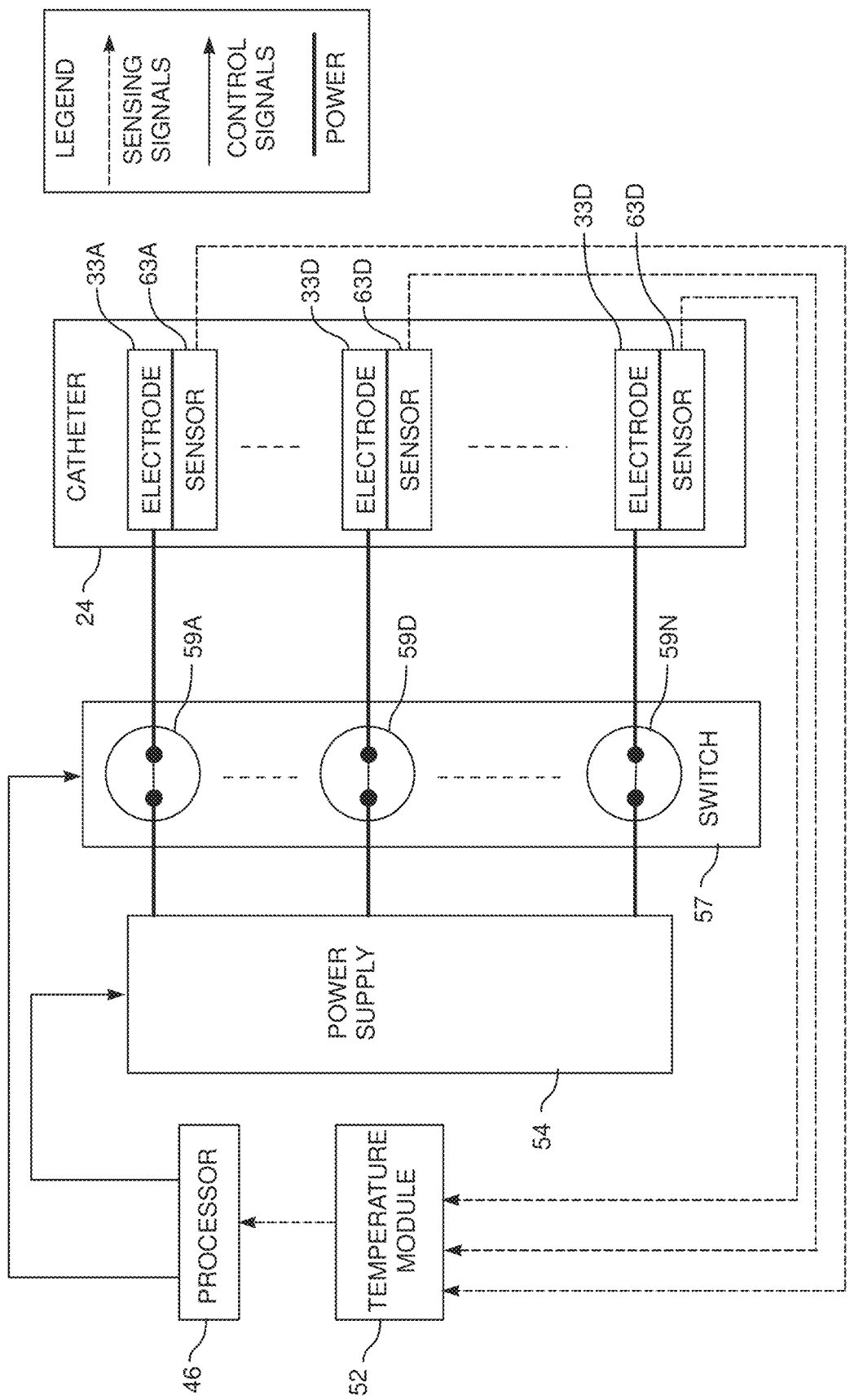
FIG. 6 is a block diagram of the apparatus of FIG. 1, according to a first embodiment of the present invention.

FIG. 6 is a block diagram of apparatus 12, according to a first embodiment of the present invention. In FIG. 6 processor 46, temperature module 52, power supply 54, switch 57, and catheter 24 are illustrated as rectangular blocks, and the block diagram also illustrates sensing signals, control signals, and power connections between the different elements of apparatus 12. Switch 57 comprises a plurality of sub-switches 59A, . . . , 59D, . . . , 59N, collectively termed sub-switches 59. Catheter 24 comprises electrodes 33A, . . . , 33D, . . . 33N, which are respectively attached to sensors 63A, . . . , 63D, . . . 63N, and which are also connected to receive power from the power supply via sub-switches 59A, . . . , 59D, . . . , 59N. In the first embodiment of apparatus 12 illustrated by FIG. 6, all sub-switches 59 are constantly closed, so that, when activated, power supply 54 supplies power simultaneously to all electrodes 33.

Thus, in operation of apparatus 12, and referring also to FIG. 1, temperature module 52 receives sensing signals from each sensor 63 of each electrode 33, and uses the signals to determine a tissue temperature, which is the temperature of the tissue surface in contact with each of the electrodes. The temperature module is configured to calculate the tissue temperature at a fixed rate, herein assumed to be every 33 ms, but other embodiments may calculate the tissue temperature at higher or lower rates. The temperature module passes the calculated tissue temperature values for each of electrodes 33 to processor 46, which in turn passes control signals to power supply 54.

Power supply 54 provides RF power, separately and individually, via respective sub-switches 59, to each electrode 33 of balloon catheter 24. In some embodiments the RF power is provided via copper wire 53. Alternatively or additionally, the RF power may be provided to the respective electrodes 33 by another conductor. The power for each electrode may be supplied in a range of 1 W to 100 W, and the power may be provided simultaneously to all electrodes 33. Thus, in an embodiment of the invention comprising twelve electrodes 33, module 54 may supply 100 W to each electrode, for an overall power input to the catheter of 1.2 kW.

In order to supply these high powers, it will be understood that leads to electrodes 33, and substrate 34, provide sufficient insulation so as to avoid any arcing from the electrodes.

In embodiments of the present invention the power supply can be configured to provide a maximum RF power to each electrode 33 that can be set within a range of 70 W-100 W. In some embodiments, the module can be configured to provide a further RF power to each electrode 33 in a different range from the maximum. In one embodiment the further power range is 20 W-60 W, and the further power is typically provided after the maximum power. The maximum RF power and the further RF power are also termed herein the first power and the second power.

The power supply also measures an impedance of each electrode 33. The impedance is measured at a predefined rate, herein assumed to be every 500 ms, but other embodiments may measure the impedance at a lower or higher rate.

For each electrode 33, the maximum power for the electrode, and the time period for which the power is delivered, is selected by professional 14. The professional may also select values of the power less than 70 W, and corresponding time periods for delivery of this reduced power. The actual power delivered by any given electrode is determined by the tissue temperature received from temperature module 52 for that electrode, as described below.

Typically, during an ablation session, the impedance presented to a given electrode 33 decreases. Embodiments of the present invention also check if the impedance presented to each electrode increases from a previous impedance measurement by more than a pre-set value, herein assumed to be 7Ω, although other embodiments may use larger or smaller values of impedance for the pre-set value. An increase of impedance typically occurs if there is an unwanted change in the tissue being ablated, such as charring or steam popping. If, for any given electrode 33, the impedance increases by more than the pre-set value, the power supply is configured to stop the RF delivery to the given electrode.

Notwithstanding the powers selected by the professional, the power supply is configured to reduce the power delivered by a given electrode, typically by between approximately 5% and approximately 958, if the tissue temperature for the given electrode, received from the temperature module, reaches or exceeds a predefined temperature threshold. The predefined temperature threshold is a maximum allowable temperature that is set by professional 14, and in the following description the predefined temperature threshold is also referred to as the maximum allowable temperature.

In one embodiment, power for a given electrode that has been originally set to 90 W is reduced to 50 W after 4 s, regardless of the reading from sensor 63. In an embodiment of the present invention, the maximum allowable temperature for all electrodes may be set within a range 60° C.-65° C. Typically, exceeding the maximum allowable tempera-ture causes undesirable effects such as charring, coagulation on an electrode 33, and/or steam pops in the tissue being ablated.

Irrigation module 58 (FIG. 1) governs the rate at which irrigation fluid is delivered to balloon catheter 24. In embodiments of the present invention it may be set within the range of 5-60 ml/min.

Figure 7:
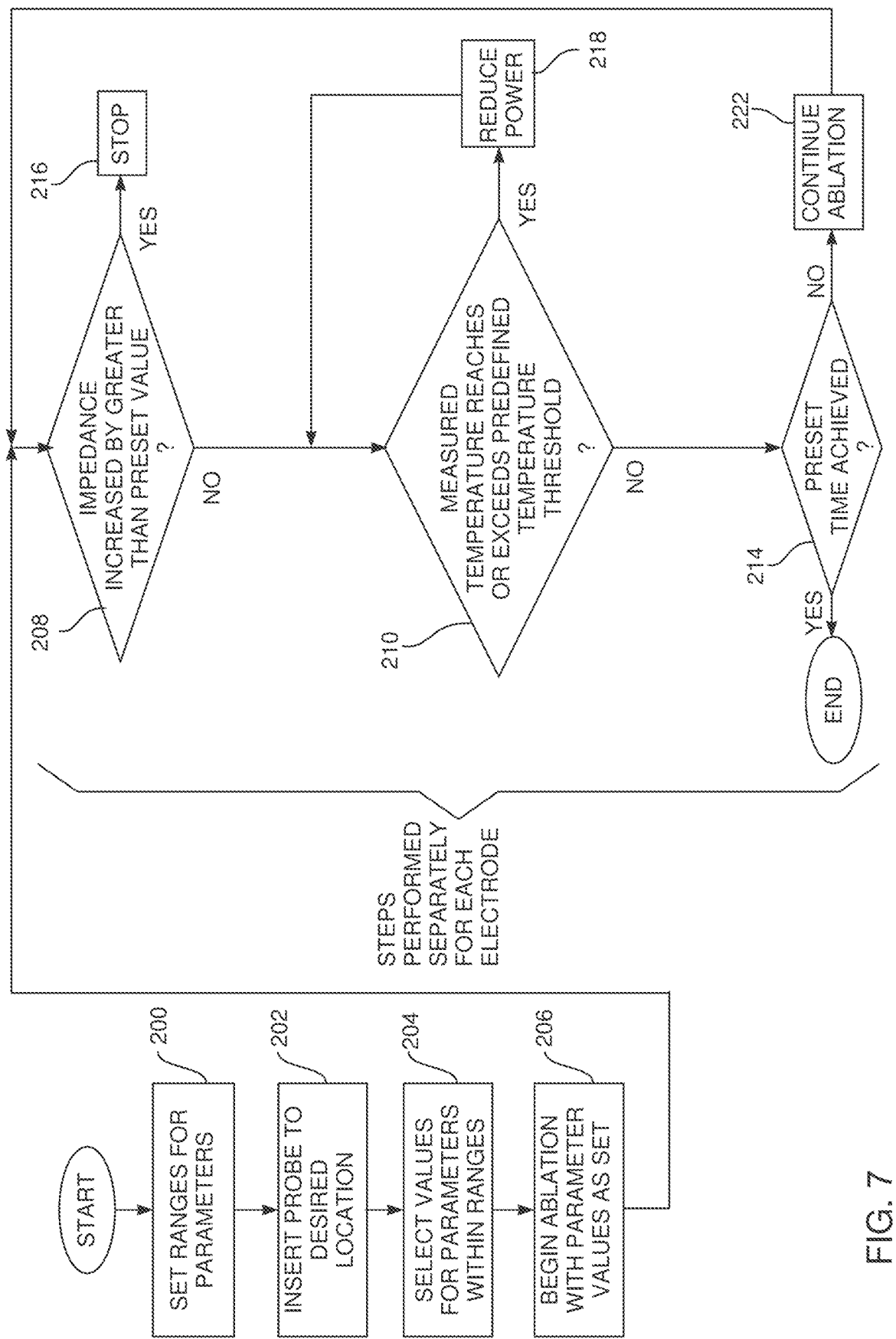
FIG. 7 is a flowchart of steps of an algorithm performed in operation of the first embodiment.

FIG. 7 is a flowchart of steps of an algorithm performed in operation of the first embodiment of apparatus 12. The steps of the flowchart assume that the block diagram of FIG. 6 applies, i.e., that all sub-switches 59 are constantly closed, so that power supply supplies power simultaneously to all electrodes 33.

In a range setting step 200, ranges for each of the variable parameters referred to above are set. The ranges may be set individually for each electrode 33. While in one embodiment this is typically the same for all electrodes, this is not necessarily the case, and in other embodiments ranges are different for different electrodes.

In one embodiment the ranges are set as shown in Table I. Typically, for the powers, an operator of apparatus 12, usually professional 14, only sets the first power, while the second power is automatically pre-set by processor 46.

TABLE I

| Parameter | Range |
| --- | --- |
| Maximum Power Delivered (First Power) | 50 W-100 W |
| Second Power | 15 W-50 W |
| Maximum allowable temperature | 50° C.-65° C. |
| Irrigation rate | 5-60 ml/min |
| First Time Period (during which First Target Power is operative) | 1 s to 6 s |
| Second Time Period (during which Second Target Power is operative) | Up to 14 s |
| Overall Time Period for Power Delivery (Sum of First and Second Time Periods) | 1 s-20 s |

Range setting step 200 is implemented before professional 14 performs an ablation.

At the beginning of an ablation session, in a probe introduction step 202, professional 14 inserts balloon catheter 24 into a desired location in myocardium 16, using the tracking system incorporated into apparatus 12.

In a select value step 204, prior to performing the ablation procedure, professional 14 selects values of the parameters listed in Table I that are to be used in the procedure, and uses controls 49 to provide the values to the system. Alternatively, the professional selects a predetermined set of the values of the parameters listed in Table I, typically by choosing a "recipe" comprising the values, from a group of such recipes. The selected values typically depend on the depth of lesion it is desired to form by the procedure. For lesions of 1-3 mm depth the inventors have found that the values of the parameters given by Table II give good results. For lesions of 4-5 mm depth the inventors have found that the values of the parameters given by Table III give good results.

It will be understood that the selections made by professional 14 in step 204 are for each electrode 33 individually. Thus for twelve electrodes 33, twelve sets of parameters are selected. While the selections may be the same for all electrodes 33, this is not a requirement. For example, the professional may select parameters according to Table II for some electrodes, and according to Table III for other electrodes.

In addition, while the selected parameters for each electrode 33 are typically applied simultaneously to all the electrodes, this is also not a requirement. Thus the parameters may be provided at least partially sequentially, and/or in a staggered fashion, e.g., 2 s after ablation has been started for one electrode, ablation may be started for a neighboring electrode.

TABLE II

Lesions of 1-3 mm Depth

| Parameter | Value |
| --- | --- |
| First Target Power | 90 W |
| Second Target Power | Not set |
| Maximum allowable temperature | 60° C. |
| Irrigation rate | 8 ml/min |
| Time Period | 4 s |

TABLE III

Lesions of 4-5 mm Depth

| Parameter | Value |
| --- | --- |
| First Target Power | 90 W |
| Second Target Power | 50 W |
| Maximum allowable temperature | 60° C. |
| Irrigation rate | 8 ml/min |
| First Time Period | 4 s |
| Second Time Period | 6 s |

Those having skill in the art will be able to determine, for other lesion depths, required values of the parameters within the ranges given by Table I, without undue experimentation.

In a begin RF delivery step 206, professional 14 operates apparatus 12, with the parameter values selected in step 204, in order to perform the ablations of electrodes 33. Typically, during the ablations, screen 62 displays values of the parameters listed in Table I to the professional. Screen 62 may also be configured to display to the professional, by methods which are known in the art, the progress of the RF deliveries to the individual electrodes. The display of the progress may be graphical, such as a simulation of the dimensions of the respective lesions as they are produced by the ablations, and/or alphanumeric.

During the RF delivery procedure processor 46 uses the temperature module and the power supply to perform a number of checks on the progress of the procedure, as shown in the flowchart by decision steps 208, 210, and 214.

Processor 46 operates steps 208-222 of the algorithm for each given electrode 33 individually and separately, measuring the impedance for the given electrode and the tissue temperature provided by sensor 63 of the electrode. For clarity, in the description below the ablations of all electrodes are assumed to be implemented simultaneously, in which case the processor performs steps 206-222 simultaneously for all the different electrodes. Those having skill in the art will be able to adapt the description, mutatis mutandis, for cases of non-simultaneous ablation.

In step 208, processor 46 uses power supply 54 to check if the impedance of a given electrode 33 has increased by more than the pre-set impedance value. If it has, the system halts the procedure for the given electrode in a termination step 216. If step 208 returns a negative value, control of the algorithm continues to decision step 210.

In step 210, the processor uses temperature module 52 to check if the measured tissue temperature for the given electrode, as measured by sensor 63 of the electrode, exceeds or reaches the predefined temperature threshold, i.e., the maximum allowable temperature selected in step 204. If decision step 210 returns a positive value, the power supply, in a reduction step 218, reduces the power to the given electrode.

The power reduction in step 218 is a function of a number of parameters:

A difference in temperature between the maximum allowable temperature T (set in step 204) and the measured temperature $T_t$ at a time t, A change of measured temperatures between sequential temperature measurements, i.e., $T_{t-1} - T_t$, A target power P, where if the flowchart is functioning in the first time period, P is the first target power, and if the flowchart is functioning in the second time period, P is the second target power, and A power $P_t$ measured at time t.

In one embodiment the following equations applies for the power reduction:

$$\Delta P(T) = \frac{a(T_{t-1} - T_t)}{T} + \frac{b(T - T_t)}{T} \quad (1)$$

where $\Delta P(T)$ is a fractional change in power as a function of temperature, and a and b are numerical constants. In a disclosed embodiment a=10 and b=1.

$$\Delta P(p) = \frac{(P - P_t)}{P} \quad (2)$$

where $\Delta P(p)$ is a fractional change in power as a function of power.

$$\Delta P = \min(\Delta P(T), \Delta P(p)) \quad (3)$$

where $\min(\Delta P(T), \Delta P(p))$ is the minimum of $\Delta P(T)$ and $\Delta P(p)$, and $\Delta P$ is the fractional change in power applied in step 218.

Typically, power reduction step 218 is performed reiteratively with decision step 210, until the measured temperature is below the predefined temperature threshold.

If step 210 returns a negative value, control continues to decision step 214.

In decision step 214, processor 46 checks if the time for the ablation by the given electrode, set in step 204, has been reached. If it has, then the flowchart ends. If the time has not been reached, control passes to a continuing ablation step 222, where the processor continues the ablation by the given electrode, and returns to decision steps 208, 210, and 214. Decision steps 208, 210, and 214 have been presented sequentially in the flowchart for simplicity and clarity. Typically, however, the system uses the power supply to perform the steps in parallel.

Second Embodiment

Figure 8:
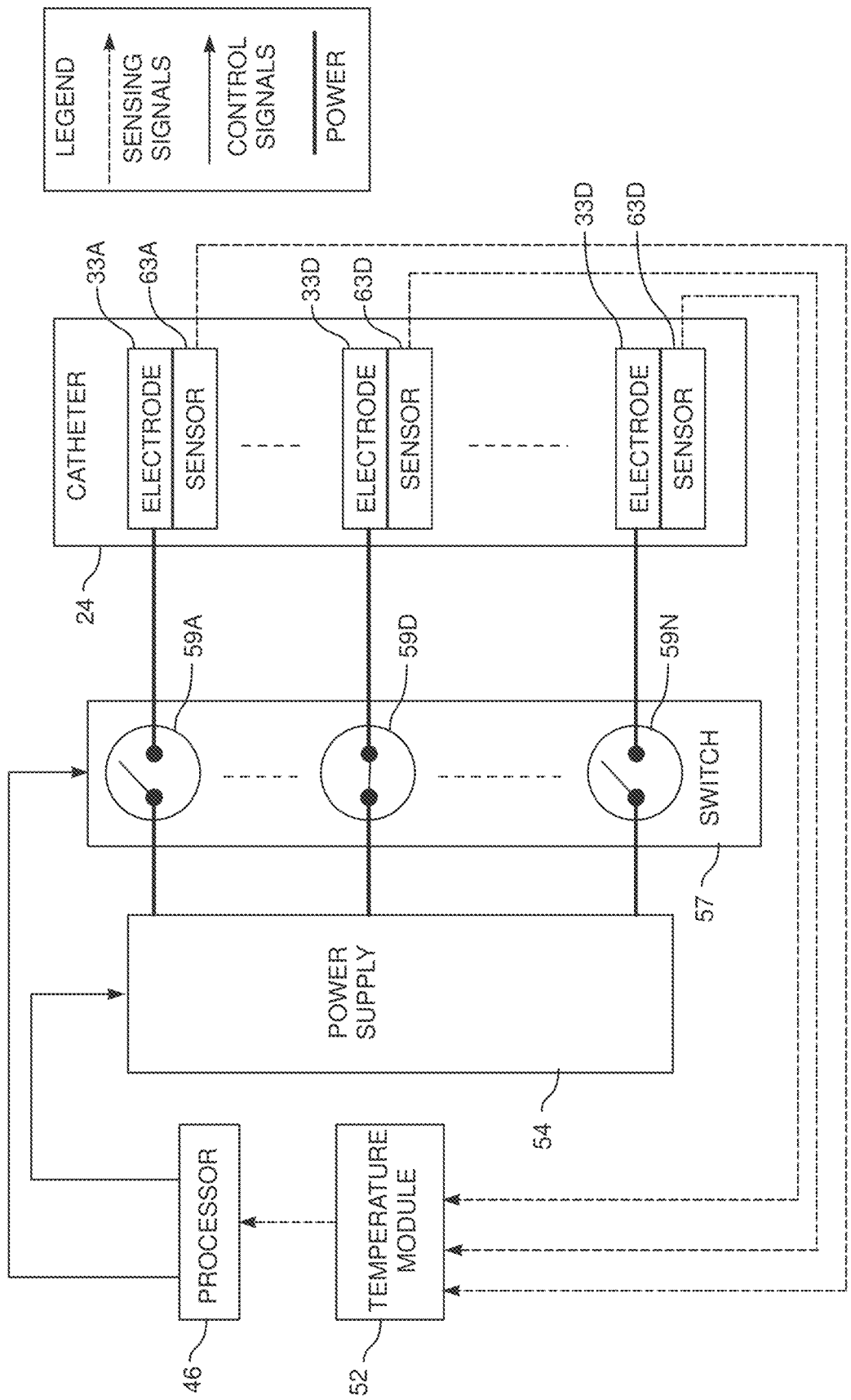
FIG. 8 is a block diagram of the apparatus of FIG. 1, according to a second embodiment of the present invention.

FIG. 8 is a block diagram of apparatus 12, according to a second embodiment of the present invention. Apart from the differences described below, the block diagram for the second embodiment is generally similar to that of the first embodiment (FIG. 6) and elements indicated by the same reference numerals in both block diagrams are common. In contrast to the first embodiment, in the second embodiment of apparatus 12 illustrated by FIG. 6, all sub-switches 59 are not constantly closed. Rather, as described in more detail below, during operation of apparatus 12 at any given instant some sub-switches 59 are open and some are closed. FIG. 8 illustrates, as an example, sub-switches 59A and 59N being open, while sub-switch 59D is closed.

Figure 9:
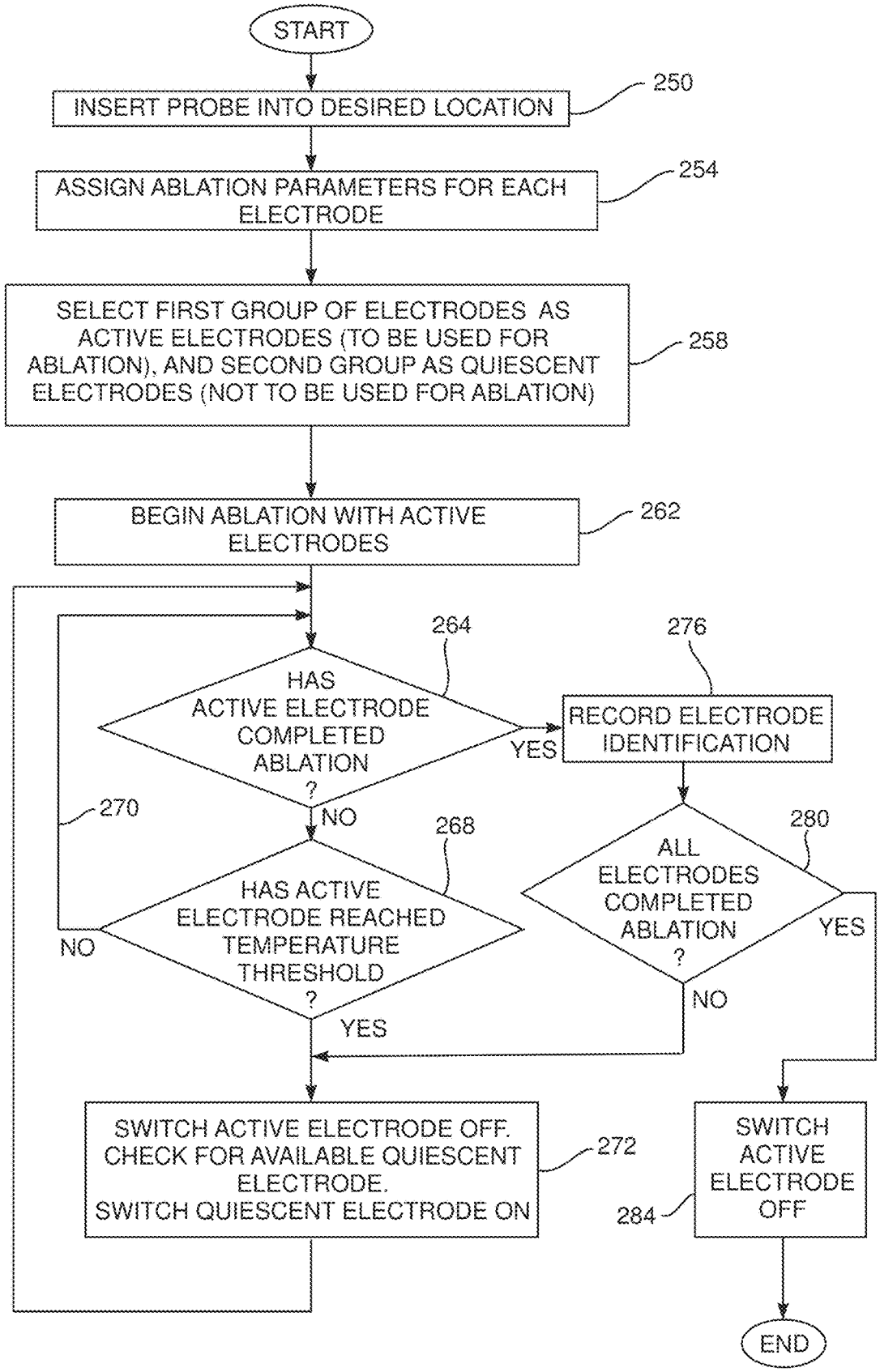
FIG. 9 is a flowchart of steps of an algorithm performed in operation of the second embodiment.

FIG. 9 is a flowchart of steps of an algorithm performed in operation of second embodiment of apparatus 12.

In contrast to the first embodiment described above, wherein power supply 54 is able to simultaneously supply ablation power to all electrodes 33, in the second embodiment described hereinbelow the power supply module is limited to being only able to supply ablation power simultaneously to a subset, i.e., a reduced number, of electrodes 33, due to a maximum power rating of the power supply.

In an initial step 250, professional 14 inserts balloon catheter 24 into a desired location in myocardium 16, using the tracking system incorporated into apparatus 12.

In an assignment step 254, the professional assigns ablation parameters individually for each electrode 33, i.e., a power to be delivered by each electrode, and a time duration for the delivery. While in some cases these may be the same for each electrode 33, e.g. 90 W for 4 s for each electrode 33, there is no requirement that this is the case. For example, electrode 33A may be assigned 80 W for 3 s, electrode 33B may be assigned 60 W for 4 s, electrode 33C may be assigned 70 W for 3 s, and so on.

In some embodiments the assignment may be determined by the positioning of catheter 24 (as implemented in step 250) with respect to tissue being ablated. E.g., if balloon catheter 24 has been positioned to contact ostium 11 of pulmonary vein 13 (FIG. 3), the power and the time may be set according to a measured or assumed thickness of the ostium section contacting respective electrodes 33.

In addition to assigning ablation parameters individually for each electrode, in step 254 a predefined temperature threshold, for the temperature measured by sensors 63, is assigned. The predefined temperature threshold may be assigned by professional 14, or alternatively may be preset for apparatus 12. The temperature threshold is, as stated above with reference to the first embodiment, a maximum allowable temperature for a given electrode 33. As is also stated above, if the temperature of tissue becomes greater than the temperature threshold, the tissue may suffer undesired effects.

In an initial ablation step 258, the professional activates apparatus 12 to begin ablation. On activation, processor 46 divides electrodes 33 into two groups: a first group, herein termed active electrodes 33, which are to be used for ablation, and a second group, herein termed quiescent electrodes 33, which are not to be used for ablation. Processor 46 may make the selection by closing or opening sub-switches 59. Thus, active electrodes 33 are selected by closing a first set of sub-switches 59, so that there is a conducting line from power supply 54 to the electrodes for these electrodes. Acquiescent electrodes 33 are selected by opening a second set of sub-switches 59, so that there is no conducting line from power supply 54 to the electrodes for these electrodes. The processor stores identities of active electrodes 33 in an active electrode register, and identities of quiescent electrodes 33 in a quiescent electrode register.

Processor 46 divides the electrodes into the two groups so that the total power required to be delivered to the active group, as determined according to the ablation parameters assigned in step 254, does not exceed a maximum power rating of power module 54. For example, if there are twelve electrodes 33, each assigned in step 254 to deliver 50 W, and module 54 has a maximum power rating of 500 W, then the processor may assign up to five electrodes to be in the active group, and the remainder, in this case seven or more, to be in the quiescent group. Typically, processor 46 assigns the active group to have the largest possible number of electrodes 33, consistent with the constraint that the maximum power rating of power module 54 is not exceeded. In some embodiments, the assignment may initially be made on a random basis. Alternatively, professional 14 may provide an indication to the processor of how the assignment is to be made on a non-random basis, for example, by providing the processor with a priority order of electrodes 33 to be assigned to the active group.

In a continuation step 262, processor 46 begins ablation by activating power supply 54, so that the module supplies power to each of electrodes 33 of the active group, i.e., to each of the electrodes having respective sub-switches 59 closed, according to the power levels set in step 254.

In a first decision step 264, processor 46 checks if a given active electrode 33 has completed its assigned ablation. For example, if in assignment step 254 a given electrode is assigned to ablate with a power 50 W for 4 s, the processor checks if an aggregate time during which the given electrode is dissipating power of 50 W is equal to 4 s. If the first decision returns negative, then the processor proceeds to a temperature decision step 268, where the processor checks, using the appropriate sensor 63, if the given active electrode temperature exceeds the temperature threshold set in step 254. If the threshold is not exceeded, i.e., the temperature condition returns negative, control returns to first decision step 264.

Thus, providing both first decision step 264 and temperature decision step 268 return negative, the processor iteratively loops through these decisions, and continues checking whether a given active electrode has completed its assigned ablation, and whether its temperature, as measured by its sensor, exceeds the temperature threshold.

Processor 46 simultaneously implements the iterative loop described above for all active electrodes. The iterative loop follows a return line 270 of the flowchart.

For any given active electrode, the iteration stops if either first decision step 264 or temperature decision step 268 returns positive, as is explained in more detail below.

If temperature decision step 268 returns positive, i.e., if a sensor 63 of an active electrode 33 being checked indicates that the threshold temperature has been exceeded, control transfers to a switch toggling step 272. Thus, if decision 268 returns positive, the iterative loop for the active electrode being checked is broken.

In switch toggling step 272 processor 46 performs the following actions:

Power to the active electrode checked prior to entry to step 272 is terminated, by the processor toggling in switch 57 the sub-switch 59 supplying the active electrode from a closed state to an open state.

Using electrode identities in the quiescent electrode register, the processor selects a quiescent electrode to be converted to an active electrode. The selection is consistent with the constraint that the maximum power rating of power module 54, when the new active electrode is operative, is not exceeded.

The selected quiescent electrode is powered on, so becoming an active electrode, by the processor toggling in switch 57 the sub-switch 59 supplying the selected electrode from an open state to a closed state.

The processor updates the active electrode register and quiescent electrode register accordingly. I.e., the identity of the electrode checked in decision step 268 is transferred from the active electrode register to the quiescent electrode register, and the identity of the quiescent electrode selected in the switch toggling step is transferred from the quiescent electrode register to the active electrode register.

Once the processor has performed the actions described above for step 272, control returns to decision step 264, so that the iterative loop of decision steps 264, 268, and line 270 restarts.

As stated above, the iterative loop may also terminate if decision step 264 returns positive. In this case the electrode being checked has completed its ablation, and control continues to a record completed electrodes step 276. In step 276 the processor transfers the identity of the electrode checked in decision step 264 from the active electrode register to a completed ablation register.

The flowchart continues to a decision step 280, wherein the processor checks the completed ablation register to see if all electrodes have completed their ablation. If step 280 returns negative, i.e., there is at least one electrode that has not completed its assigned ablation, control continues to switch toggling step 272, described above, wherein the active electrode checked in condition 264 is switched off, and an available quiescent electrode is switched on.

If step 280 returns positive, i.e., all electrodes have completed their ablation, then the active electrode checked in decision step 264, which is the last operative electrode, is switched off in a final flowchart step 284, and the flowchart ends.

While the description above has used a balloon catheter to provide multiple electrodes 33 for respective ablations, it will be understood that embodiments of the present invention are not limited to balloon catheters. Thus embodiments of the present invention comprise other catheters, such as basket catheters, lasso catheters, and focal catheters, with multiple electrodes that are used for respective ablations.

It will thus be appreciated that the embodiments described above are cited by way of example, and that the invention is not limited to what has been present particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A system comprising:
a power supply configured to supply radiofrequency (RF) ablation energy to each of a plurality of electrodes deployed on a catheter so as to ablate tissue of an organ in contact with a respective one of the plurality of electrodes, each of the plurality of electrodes having a temperature sensor;
a temperature module configured to determine a temperature of the surface of the organ tissue in contact with each of the plurality of electrodes in response to receiving sensing signals from each of the electrode temperature sensors;
one or more processors coupled to the power supply and the temperature module;
a non-transitory computer readable medium storing a plurality of instructions, which when executed, cause the one or more processors to:
i) receive a predefined power of RF ablation energy to be delivered by each of the plurality of electrodes, a predefined time duration for delivering the predefined power by each of the plurality of electrodes and a predefined temperature threshold of the surface of the tissue in contact with each of the plurality of electrodes,
ii) identify an active group of the plurality of electrodes to be used for ablation and an inactive group of the plurality of electrodes, wherein a sum of the pre-determined power to be delivered by each electrode in the active group of electrodes does not exceed a maximum power of the power supply,
iii) cause the power supply to continue delivering power to each electrode in the active group of electrodes that has not delivered the predefined power for the predefined time duration when the temperature of the tissue in contact with the respective electrode does not exceed the temperature threshold,
iv) cause each electrode in the active group of electrodes that has not delivered the predefined power for the predefined time duration to become inactive when the temperature of the tissue in contact with the respective electrode exceeds the temperature threshold,
v) identify, in response to an electrode in the active group of electrodes becoming inactive, an electrode in the inactive group of electrodes to become active such that sum of the pre-determined power to be delivered by each electrode in the active group of electrodes does not exceed the maximum power of the power supply, and
vi) cause each electrode in the active group of electrodes that has delivered the predefined power for the predefined time duration to become inactive.

2. The apparatus according to claim 1, wherein the plurality of electrodes comprises up to twelve electrodes, and wherein the power supply is configured to provide up to 1.2 kW of radiofrequency power.

3. The apparatus according to claim 1, wherein the catheter comprises a balloon catheter.

4. The apparatus according to claim 1, wherein the catheter comprises a basket catheter.

5. A method, comprising:
receiving, by a processor coupled to a power supply and a temperature module, a predefined power of radiofrequency (RF) ablation energy to be delivered by each of a plurality of electrodes deployed on a catheter, a predefined time duration for delivering the predefined power by each of the plurality of electrodes and a predefined temperature threshold of a surface of organ tissue in contact with a respective one of the plurality of electrodes, the temperature module being configured to determine a temperature of the tissue surface in in contact with each of the plurality of electrodes in response to receiving sensing signals from temperature sensors in each of the plurality of electrodes, respectively;
identifying an active group of the plurality of electrodes to be used for ablation and an inactive group of the plurality of electrodes, wherein a sum of the pre-determined power to be delivered by each electrode in the active group of electrodes does not exceed a maximum power of the power supply;
causing the power supply to continue delivering power to each electrode in the active group of electrodes that has not delivered the predefined power for the predefined time duration when the temperature of the tissue in contact with the respective electrode does not exceed the temperature threshold;

causing each electrode in the active group of electrodes that has not delivered the predefined power for the predefined time duration to become inactive when the temperature of the tissue in contact with the respective electrode exceeds the temperature threshold;

identifying, in response to an electrode in the active group of electrodes becoming inactive, an electrode in the inactive group of electrodes to become active such that sum of the pre-determined power to be delivered by each electrode in the active group of electrodes does not exceed the maximum power of the power supply; and causing each electrode in the active group of electrodes that has delivered the predefined power for the predefined time duration to become inactive.

6. The method according to claim 5, wherein the plurality of electrodes comprises up to twelve electrodes, and wherein the power supply is configured to provide up to 1.2 kW of radiofrequency power.

7. The method according to claim 5, wherein the catheter comprises a balloon catheter.

8. The method according to claim 5, wherein the catheter comprises a basket catheter.

9. A computer program product, comprising a non-transitory computer-readable medium having computer-readable program code embodied therein to be executed by one or more processors coupled to a power supply and a temperature module, the program code including instructions to:

receive a predefined power of radiofrequency (RF) ablation energy to be delivered by each of a plurality of electrodes deployed on a catheter, a predefined time duration for delivering the predefined power by each of the plurality of electrodes and a predefined temperature threshold of a surface of organ tissue in contact with a respective one of the plurality of electrodes, the temperature module being configured to determine a temperature of the tissue surface in in contact with each of the plurality of electrodes in response to receiving sensing signals from temperature sensors in each of the plurality of electrodes, respectively;

identify an active group of the plurality of electrodes to be used for ablation and an inactive group of the plurality of electrodes, wherein a sum of the pre-determined power to be delivered by each electrode in the active group of electrodes does not exceed a maximum power of the power supply;

cause the power supply to continue delivering power to each electrode in the active group of electrodes that has not delivered the predefined power for the predefined time duration when the temperature of the tissue in contact with the respective electrode in the active group of electrodes does not exceed the temperature threshold;

cause each electrode in the active group of electrodes that has not delivered the predefined power for the predefined time duration to become inactive when the temperature of the tissue in contact with the respective electrode in the active group of electrodes exceeds the temperature threshold;

identify, in response to an electrode in the active group of electrodes becoming inactive, an electrode in the inactive group of electrodes to become active such that sum of the pre-determined power to be delivered by each electrode in the active group of electrodes does not exceed the maximum power of the power supply; and cause each electrode in the active group of electrodes that has delivered the predefined power for the predefined time duration to become inactive.

10. The computer program product according to claim 9, wherein the plurality of electrodes comprises up to twelve electrodes, and wherein the power supply is configured to provide up to 1.2 kW of radiofrequency power.

11. The computer program product according to claim 9, wherein the catheter comprises a balloon catheter.

12. The computer program product according to claim 9, wherein the catheter comprises a basket catheter.

* * * * *